United States Patent
Fan et al.

(10) Patent No.: US 12,173,373 B2
(45) Date of Patent: Dec. 24, 2024

(54) SCREENING METHOD FOR HOMOZYGOUS GENOTYPE AGOUTI HAIR COLOR RABBITS

(71) Applicants: SHANDONG AGRICULTURAL UNIVERSITY, Shandong (CN); QINGDAO KANGDA RABBIT INDUSTRY DEVELOPMENT CO., LTD., Shandong (CN)

(72) Inventors: Xinzhong Fan, Shandong (CN); Yongxu Liu, Shandong (CN); Xibo Qiao, Shandong (CN); Chunhui Hui, Shandong (CN); Hong Zhao, Shandong (CN); Mingyong Li, Shandong (CN); Bo Wang, Shandong (CN); Aiguo Yang, Shandong (CN); Jiaqing Hu, Shandong (CN)

(73) Assignees: SHANDONG AGRICULTURAL UNIVERSITY, Tai'an (CN); QINGDAO KANGDA RABBIT INDUSTRY DEVELOPMENT CO., LTD., Qingdao (CN)

( * ) Notice: Subject to any disclaimer, the term of this patent is extended or adjusted under 35 U.S.C. 154(b) by 883 days.

(21) Appl. No.: 17/239,695

(22) Filed: Apr. 26, 2021

(65) Prior Publication Data

US 2021/0246516 A1   Aug. 12, 2021

Related U.S. Application Data

(63) Continuation-in-part of application No. PCT/CN2020/071076, filed on Jan. 9, 2020.

(30) Foreign Application Priority Data

Jan. 11, 2019   (CN) .......................... 201910029901.6

(51) Int. Cl.
*C12Q 1/6888*   (2018.01)
*A01K 67/02*   (2006.01)

(52) U.S. Cl.
CPC ............ *C12Q 1/6888* (2013.01); *A01K 67/02* (2013.01); *C12Q 2600/124* (2013.01); *C12Q 2600/156* (2013.01)

(58) Field of Classification Search
CPC ........ C12Q 2600/156; C12Q 2600/124; C12Q 1/6888; A01K 67/02
See application file for complete search history.

(56) References Cited

PUBLICATIONS

Fontanesi, L., "The rabbit in the genomics era: Applications and perspectives in rabbit biology and breeding," Proceedings of the 11th World Rabbit Congress, pp. 1-21 (Year: 2016).*
Fontanesi et al., "Characterization of the rabbit agouti signaling protein (ASIP) gene: Transcripts and phylogenetic analyses and identification of the causative mutation of the nonagouti black coat colour," Genomics, vol. 95, pp. 166-175. (Year: 2010).*
Yaoju Duan, Research and Analysis of the Candidate Gene MC1R, AGOUTI, TYR, TYRP1 and MLPH of Rabbits' Color, Chinese Master's Theses Full-text Database, Feb. 15, 2018.
Cui-Jun Yang et al., Effects of agouti gene mutation and protein structure changes of ASIP on hair colour in colour Rex rabbit, Acta Agriculturae Zhejiangensis, Dec. 31, 2015, pp. 2071-2077, vol. 27, No. 12.
L. Fontanesi et al., Mutations in the melanocortin 1 receptor (MC1R) gene are associated with coat colours in the domestic rabbit (*Oryctolagus cuniculus*), Animal Genetics, Dec. 31, 2006, pp. 489-493, vol. 37.
Bernhard Aigner et al., Tyrosinase gene variants in different rabbit strains, Mammalian Genome, Dec. 31, 2000, pp. 700-702, vol. 11.
International Search Report of PCT Patent Application No. PCT/CN2020/071076 issued on Apr. 9, 2020.

* cited by examiner

*Primary Examiner* — Young J Kim

(57) ABSTRACT

The invention provides a selecting method for domestic rabbits with a agouti/Belgian hair color based on homozygous genotype selection. The purification method is applicable to purification of various domestic rabbits with the agouti/Belgian hair color. The method includes the following steps: firstly, selecting the domestic rabbits with a hair color phenotype which is the agouti/Belgian hair color; then detecting an ASIP gene, a MC1R gene and a TYR gene at the same time by utilizing a first primer set, a second primer set and a third primer set; screening the domestic rabbits with genotypes of AA (corresponding to the ASIP gene), EE (corresponding to the MC1R gene) and CC (corresponding to the TYR gene). The domestic rabbits with the genotype of AAEECC, which are obtained by the screening method of the invention, are agouti/Belgian hair color homozygotes and the recessive white gene is eliminated.

6 Claims, 4 Drawing Sheets
Specification includes a Sequence Listing.

SCREENING METHOD FOR HOMOZYGOUS GENOTYPE AGOUTI HAIR COLOR RABBITS

CROSS-REFERENCE TO RELATED APPLICATION

The present application is a Continuation-In-Part Application of PCT Application No. PCT/CN2020/071076 filed on Jan. 9, 2020, which claims the benefit of Chinese Patent Application No. 201910029901.6 filed on Jan. 11, 2019. The contents of the above are hereby incorporated by reference in their entirety.

REFERENCE TO SEQUENCE LISTING

A Sequence Listing is submitted as an ASCII formatted text file via EFS-Web, with a file name of "Sequence-_Listings_SCH-21021-USPT.TXT", a creation date of Apr. 26, 2021, and a size of 2,646 bytes. The Sequence Listing filed via EFS-Web is part of the specification and is incorporated in its entirety by reference herein.

FIELD OF THE INVENTION

The present invention relates to the field of livestock breeding, and specifically relates to a screening method for domestic rabbits with an agouti hair color based on homozygous genotype selection.

BACKGROUND OF THE INVENTION

The hair color of the Belgian rabbit is a wild type character. Its coat is dark red with yellowish brown or reddish brown. Both ends of the whole hair are deep colored and in the middle it is lighter, the hair has a firm texture and is close to the body surface. The hair fibers of the head, neck, back, body sides, and the outer part of the limbs are all similar in color to rabbit hair fibers. The hair fibers have light gray color in the base, and slightly lighter color in the middle part, with darker hair tips, and mixed with black bristle. The lower jaw, the lower neck, the inner part of the limbs, the abdomen, and the ventral surface of the tail are lighter in color. Except for the yellowish brown color on the abdomen, the inner side of the limbs and the submandibular, other parts' hair is dark gray, and the color of the coat is very bright. Belgian rabbit hair color has a natural gloss, its fur is large, and the leather is flexible and elastic, and thus is favored by the market.

The agouti/Belgian hair color can not only be used as an easily recognizable characteristic of domestic rabbit breeds, but also has specific economic value, social needs and market preferences. The hair color of rabbits is controlled by multiple genes, and these genes have presented complex interactions of dominant and recessive and epistatic interactions. In the practice, the genetic background of the hair color of the Belgian rabbits is relatively complicated, and there are few populations that are homozygous for the hair color. When using conventional breeding methods, purification of hair color is not only time-consuming and laborious, but also often not thorough enough. Most agouti/Belgian hair color rabbit populations carry the recessive white genes, and white-color individuals often appear in the offspring generation. This problem is particularly prominent in the hybrid production of agouti/Belgian hair colored rabbit breeds and white rabbit breeds. In purebred breeding and hybrid production of domestic rabbits, since we cannot control the separation and recombination of hair color genes in the rabbits breeding process, specific genes must be selected in advance through breeding design for hair color genotypes to obtain offspring with consistent hair color with particular types of homozygous parent population.

SUMMARY OF THE INVENTION

In order to solve the problems existing in the prior art, the present invention provides a method for selecting for domestic rabbits with an agouti hair color based on homozygous genotype selection. The method of the invention is as follows: first selecting the rabbits with the agouti/Belgian hair color phenotype; then use the first primer set, the second primer set, and the third primer set to simultaneously detect the ASIP gene, the MC1R gene and the TYR gene, to select the agouti/Belgian hair color rabbits with genotypes of AA (corresponding to ASIP gene), EE (corresponding to MC1R gene) and CC (corresponding to TYR gene).

The technical solution adopted by the present invention is:

In the present invention, the genes used include ASIP gene, MC1R gene and TYR gene.

The ASIP gene, which is commonly referred to as the Agouti gene, is "Agouti hair color gene" or "mouse gray gene" in Chinese language. Its structure is complex, not a single locus, but a locus comprising many alleles, consisting of 4 exons and 3 introns. Exons 2, 3, and 4 are coding sequences, and exon 1 is a non-coding sequence. The ASIP gene encodes a paracrine signaling molecule, i.e. Agouti signaling protein (ASIP), which enables melanocytes in hair follicles to synthesize pheomelanin. In addition, the ASIP gene also encodes an Agouti gene-related protein, regulating hair colors together with ASIP.

The melanocortin 1-receptor (MC1R) gene plays an important role in controlling the formation of melanin. MC1R is one of the G protein-coupled receptors in the melanocortin receptor family and is the smallest receptor among its family members. Its encoded protein mainly acts on melanocytes, and it combines with α-MSH (alpha melanocyte stimulating hormone receptor) to increase the level of cyclic adenosine monophosphate to form eumelanin. Different MC1R genotypes of domestic rabbits correspond to different hair colors.

ASIP and MC1R are two important candidate genes for regulating hair color in mammals. The expression of ASIP will cause the production of pheomelanin, and the expression of MC1R will cause the production of eumelanin, by adjusting the ratio of eumelanin to pheomelanin to affect the hair color.

The tyrosinase (TYR) gene is located on an autosome. The trait controlled by the normal TYR gene is colored hair. When the base at position 1119 in the TYR gene is mutated from "C" to "A", it is recessive white genotype.

According to the primer sets for purifying Belgian colored hair rabbits according to the present invention, as shown in SEQ ID NO. 5 and SEQ ID NO. 6, the forward primer of the third primer set is 5'-AAGACAAGGTGAAAGG-3' as set forth in SEQ ID NO. 5, the reverse primer is 5'-TAAATC-CAATAGGCAC-3' as set forth in SEQ ID NO. 6.

A method for selecting a homozygous genotype agouti/Belgian hair color rabbit, the method comprising the following steps:

(1) extracting the genomic DNA of the domestic rabbit to be identified, and using a first primer set, a second primer set and a third primer set to amplify to obtain the amplified gene product. The first primer set is used to detect the base sequence of the ASIP gene, the second primer set is used to detect the base sequence of MC1R gene, and the third primer set is used to detect the base sequence of TYR gene; and (2) according to the amplified gene product obtained in step (1), identifying the genotype of the domestic rabbit to be identified, and the homozygous rabbit with the agouti/Belgian hair color phenotype is obtained by selecting.

Further, in step (1), the rabbit to be identified is any one of meat rabbits, rex rabbits, longhair rabbits, or ornamental rabbits.

Further, in step (1), the phenotype of the hair color of the domestic rabbit to be identified is agouti/Belgian hair color.

Further, in step (1), a forward primer of the first primer set is 5'-AAGAAAGCAGGAAGGCACA-3' as set forth in SEQ ID NO. 1, and a reverse primer is 5'-CAAGGCAGGATTGGCTCA-3' as set forth in SEQ ID NO. 2.

Further, in step (1), a forward primer of the second primer set is 5'-ACCTGCTGGTGAGCGTGA-3' as set forth in SEQ ID NO. 3, and a reverse primer is 5'-GTAGCGCAGTGCGTAGAAGA-3' as set forth in SEQ ID NO. 4.

Further, in step (1), a forward primer of the third primer set is 5'-AAGACAAGGTGAAAGG-3' as set forth in SEQ ID NO. 5, and a reverse primer is 5'-TAAATC-CAATAGGCAC-3' as set forth in SEQ ID NO. 6.

Further, in step (1), when the first primer set is used for amplification, an amplification system is: a total volume of 20 µL, including Tris-HCL 33.5 mM, MgCl$_2$ 25 mM, dNTPs 0.2 mM, forward primers and reverse primers are 5 ng/µl respectively, Taq DNA polymerase 2.5 U, and template DNA 50 ng; an amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then a PCR amplification program is completed and storing obtained products at 4° C.

Further, in step (1), when the second primer set is used for amplification, an amplification system is: a total volume of 20 µL, including Tris-HCL 33.5 mM, (NH$_4$)$_2$SO$_4$ 8.0 mM, MgCl$_2$ 1.5 mM, TWEEN-20 0.05%, dNTPs 0.2 mM, the forward primer and the reverse primer are 3.3 ng/µl respectively, Taq DNA polymerase 2.0 U and template DNA 50 ng; an amplification procedure is: pre-denaturation at 94° C. for 2 min; then proceeding 30 cycles of the following steps: denaturation at 94° C. for 45 s, annealing at 62° C. for 45 s, extending at 72° C. for 60 s; after completing the 30 cycles, extending at 72° C. for 8 min, then a PCR amplification program is completed and storing obtained products at 4° C.

Further, in step (1), when the third primer set is used for amplification, an amplification system is: a total volume of 20 µL, including Tris-HCL 33.5 mM, MgCl$_2$ 25 mM, dNTPs 0.2 mM, the forward primer and the reverse primer are 5 ng/µl respectively, Taq DNA polymerase 2.5 U, and template DNA 50 ng; an amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then a PCR amplification program is completed and storing obtained products at 4° C.

Further, in step (1), phenol-chloroform extraction method or CTAB method is used to extract the genomic DNA of the domestic rabbit to be identified.

Further, in step (2), an identification method is: sequencing the amplified products obtained by using the first primer set, and if a base "A" is detected as an insertion between a 5th position and a 6th position of a second exon of the ASIP gene, it is recorded as Genotype "a", and when the base "A" is not detected, it is recorded as Genotype "A";

Sequencing the amplified products obtained by using the second primer set, and if there is no deletion of bases at positions 280-285 of the MC1R gene and a 30 bp deletion of bases at positions 304-333 is detected, it is recorded as Genotype "E"; and Sequencing the amplified products obtained by using the third primer set, and detecting a base type at position 1119 of a fourth exon of the TYR gene, when the base is "C", it means that no gene mutation has occurred, thus it is recorded as Genotype "C"; when the base is "A", it means that a gene mutation has occurred, and it is recorded as Genotype "c".

Further, in step (2), the application of the homozygous agouti/Belgian hair color rabbit with the genotype AACCEE in breeding is selected.

Using the above primer sets and the identification methods, the ASIP gene, the MC1R gene and the TYR gene can be detected at the same time, and the homozygous agouti/Belgian hair color rabbit with the genotypes of AA (corresponding to ASIP gene), EE (corresponding to MC1R gene) and CC (corresponding to TYR gene) are selected.

On the other hand, the present invention also provides a breeding method for agouti/Belgian hair color rabbits, comprising selecting homozygous genotype agouti/Belgian hair color rabbits by using the above-mentioned method.

The beneficial effects of the present invention are:

The present invention provides a method for selecting homozygous genotype agouti/Belgian hair color rabbits, and the method is suitable for the purification of various breeds of agouti/Belgian hair color rabbits, such as meat rabbits, rex rabbits, long-hair rabbits, and ornamental rabbits. The method of the present invention is as follows: first selecting the rabbits with the agouti/Belgian hair color phenotype; then using the first primer set, the second primer set and the third primer set to simultaneously detect the ASIP gene, the MC1R gene and the TYR gene, and the rabbits with genotypes AA (corresponding to ASIP gene), EE (corresponding to MC1R gene) and CC (corresponding to TYR gene) are selected. The rabbits obtained by the method of the present invention are homozygous, and the recessive white gene is eliminated, and at the same time, the double check of the homozygosity of the dominant Belgian coat color gene and the purification of the recessive white gene is realized. The agouti/Belgian hair color rabbit breeds cultivated by the method of the present invention can not only ensure that the offspring will not appear to be white individuals when bred with the white rabbit breed, but also ensure the uniformity of the phenotype of the rabbits, thus ensuring the consistency of the products of breeding companies. On this basis, the germplasm materials of breeding enterprises are well protected.

BRIEF DESCRIPTION OF THE DRAWINGS

In order to illustrate the examples of the present invention or the technical solutions in the prior art more clearly, the following will briefly introduce the drawings that need to be used in the description of the examples or prior art. Obviously, the drawings in the following description are only some examples of the present invention. For those of ordinary skill in the art, other drawings can be obtained based on these drawings without creative work.

DETAILED DESCRIPTION OF THE INVENTION

Figure 1:
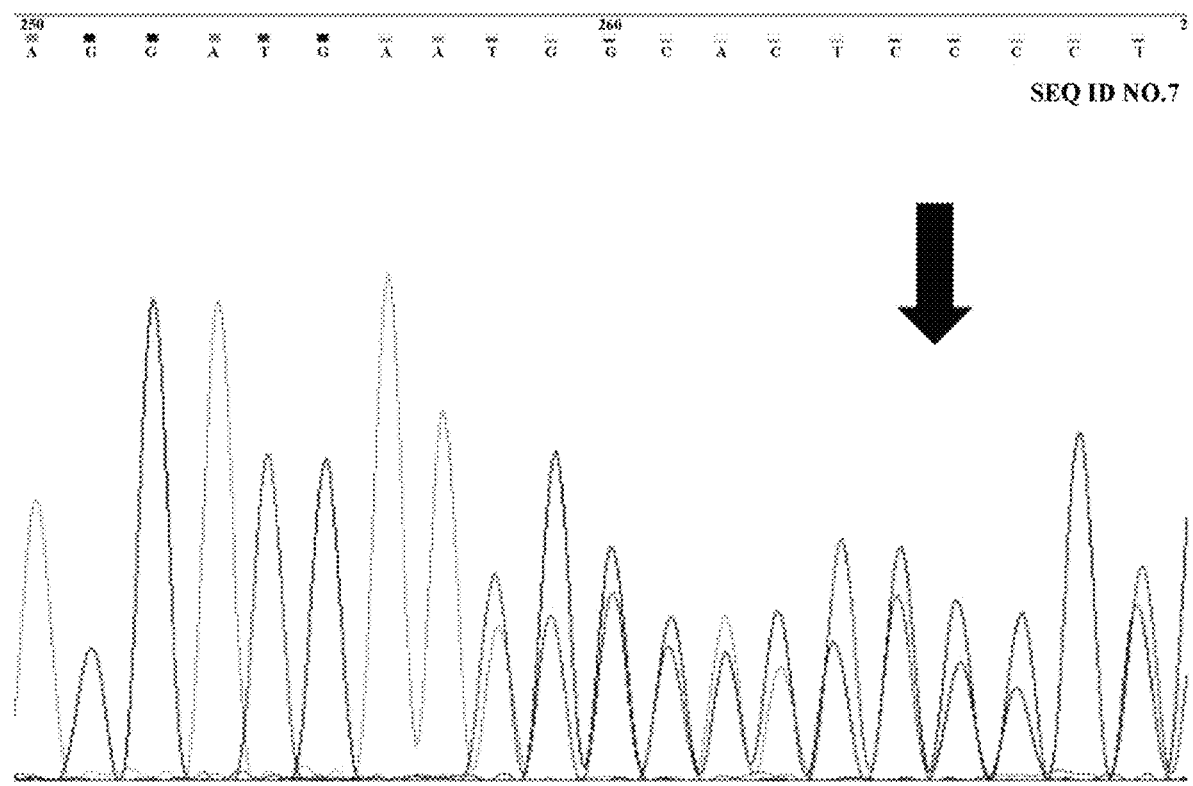
FIG. 1 is a diagram of the amplified fragments of the ASIP gene in Example 1, wherein the sequence (SEQ ID NO. 7) in the upper part of FIG. 1 is the corresponding base sequence determined according to the sequencing peak map.

In order to make the purpose, technical solutions and advantages of the present invention to be clear, the present invention is further described in detail below. Obviously, the described examples are only a part of the examples of the present invention, rather than all the examples. Based on the examples of the present invention, all other implementation manners obtained by those of ordinary skill in the art without creative work shall fall within the protection scope of the present invention.

Example 1

The method for selecting homozygous genotype of agouti/Belgian hair color domestic rabbits, comprising the following steps:

1. Extracting the genomic DNA of agouti/Belgian hair color meat rabbits, and using the first primer set, the second primer set and the third primer set to amplify to obtain the amplified products;

The designed primers of this example are shown in Table 1;

TABLE 1

Primer Set Sequences

| Primers | Primer sequence | Length of the product |
|---|---|---|
| The forward primer of the 1st primer set | 5'-AAGAAAGCAGGAAGGCACA-3' (SEQ ID NO.1) | 600 bp |
| The reverse primer of the 1st primer set | 5'-CAAGGCAGGATTGGCTCA-3' (SEQ ID NO.2) | |
| The forward primer of the 2nd primer set | 5'-ACCTGCTGGTGAGCGTGA-3' (SEQ ID NO.3) | 620 bp |
| The reverse primer of the 2nd primer set | 5'-GTAGCGCAGTGCGTAGAAGA-3' (SEQ ID NO.4) | |
| The forward primer of the 3rd primer set | 5'-AAGACAAGGTGAAAGG-3' (SEQ ID NO.5) | 488 bp |

TABLE 1-continued

Primer Set Sequences

| Primers | Primer sequence | Length of the product |
|---|---|---|
| The reverse primer of the 3rd primer set | 5'-TAAATCCAATAGGCAC-3' (SEQ ID NO.6) | |

When the first primer set is used for amplification, the amplification system is: a total volume of 20 μL, including Tris-HCL 33.5 mM, MgCl$_2$ 25 mM, dNTPs 0.2 mM, the forward primers and the reverse primers are 5 ng/μl respectively, Taq DNA polymerase 2.5 U, and template DNA 50 ng; the amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then the PCR amplification program is completed and storing the obtained products at 4° C.

When the second primer set is used for amplification, the amplification system is: a total volume of 20 μL, including Tris-HCL 33.5 mM, (NH$_4$)$_2$SO$_4$ 8.0 mM, MgCl$_2$ 1.5 mM, TWEEN-20 0.05%, dNTPs 0.2 mM, the forward primer and the reverse primer are 3.3 ng/μl respectively, Taq DNA polymerase 2.0 U and template DNA 50 ng; the amplification procedure is: pre-denaturation at 94° C. for 2 min; then proceeding 30 cycles of the following steps: denaturation at 94° C. for 45 s, annealing at 62° C. for 45 s, extending at 72° C. for 60 s; after completing the 30 cycles, extending at 72° C. for 8 min, then the PCR amplification program is completed and storing the obtained products at 4° C.

When the third primer set is used for amplification, the amplification system is: a total volume of 20 μL, including Tris-HCL 33.5 mM, MgCl$_2$ 25 mM, dNTPs 0.2 mM, the forward primer and the reverse primer are 5 ng/μl respectively, Taq DNA polymerase 2.5 U, and template DNA 50 ng; the amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then the PCR amplification program is completed and storing the obtained products at 4° C.

2. According to the amplified product obtained in step (1), identifying the genotype of the agouti/Belgian hair color meat rabbit, and selecting for the homozygous agouti/Belgian hair color meat rabbit. The specific selecting method is as follows:

sequencing the amplified product obtained by using the first primer set, and if a base "A" is detected as the insertion between the 5th position and the 6th position of the second exon of the ASIP gene, it is recorded as Genotype "a", and when the base "A" is not detected, it is recorded as Genotype "A"; sequencing the amplified product obtained by using the second primer set, and if there is no deletion of bases at positions 280-285 of the MC1R gene and a 30 bp deletion of bases at positions 304-333 is detected, it is recorded as Genotype "E"; sequencing the amplified product obtained by using the third primer set, and detecting the base type at position 1119 of the fourth exon of the TYR gene, when the base is "C", it means that no gene mutation has occurred, thus it is recorded as Genotype "C"; when the base is "A", it means that a gene mutation has occurred, and it is recorded as Genotype "c".

3. After selecting for and obtaining homozygous agouti/Belgian hair color meat rabbits, establishing a basic pool of homozygous agouti/Belgian hair color meat rabbits.

Using the above primer sets and the identification method, the ASIP gene, the MC1R gene and the TYR gene can be detected at the same time, and the domestic rabbits with the genotypes of "AA" (corresponding to ASIP gene), "EE" (corresponding to MC1R gene) and "CC" (corresponding to TYR gene) are selected. The hybridization of male and female rabbits with genotype "AAEECC" can establish a homozygous agouti/Belgian hair color domestic rabbit population. Correspondingly, the agouti/Belgian hair color heterozygotes with the genotypes "Aa" and "Ee" and the individuals carrying the recessive white gene with the genotypes "Cc" and "cc" can be eliminated to achieve the purification of the agouti/Belgian hair color domestic rabbits. The rabbits obtained by the method of the present invention are homozygous, and the recessive white gene is eliminated. When hybridizing with other breeds, it not only ensures that no white hair color offspring will be born, but also ensures the uniformity of the rabbit phenotype. Under the condition of ensuring the products consistency of the breeding enterprises, the breeding materials of breeding enterprises are well protected.

The first primer set is used to amplify the ASIP gene fragment, as shown by the position indicated by the arrow in FIG. 1. It can be clearly seen that there are overlapping peaks at the pointing place, indicating that there are multiple bases at this position and there is a genetic mutation with a mutation Genotype "a".

Figure 2:
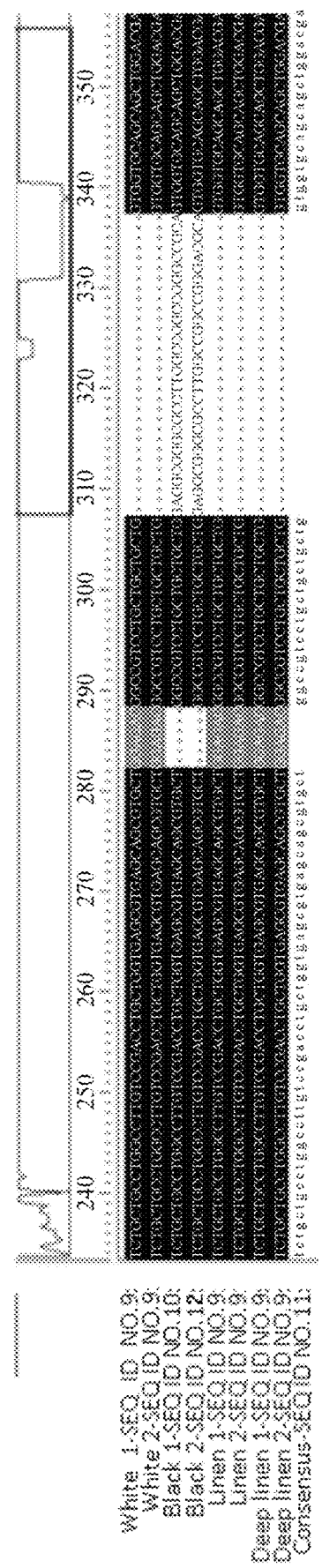
FIG. 2 is a diagram showing the sequence detection of the MC1R gene in Example 1, wherein 9 base sequences are fragments of the MC1R gene sequence of rabbits with different hair colors, the 9 sequences from top to bottom include SEQ ID NO. 9 of white 1, SEQ ID NO. 9 of white 2, SEQ ID NO. 10 of black 1, SEQ ID NO. 12 of black 2, SEQ ID NO. 9 of linen 1, SEQ ID NO. 9 of linen 2, SEQ ID NO. 9 of deep linen 1, SEQ ID NO. 9 of deep linen 2, and SEQ ID NO. 11 of consensus sequence.

The second primer set is used to amplify the MC1R gene fragment. As shown in FIG. 2, the bases at positions 280-285 of the MC1R gene are not deleted, and there are 30 bp bases deletion at positions 304-333, thus it is Genotype "E". It should be noted that the sequencing is based on the sequence of the MC1R gene, to check whether the bases at positions 280-285 and 304-333 of the MC1R gene are missing, but not to check whether the bases at positions 280-285 and 304-333 of the amplified sequence (the length of the amplified product is 620 bp).

Figure 3:
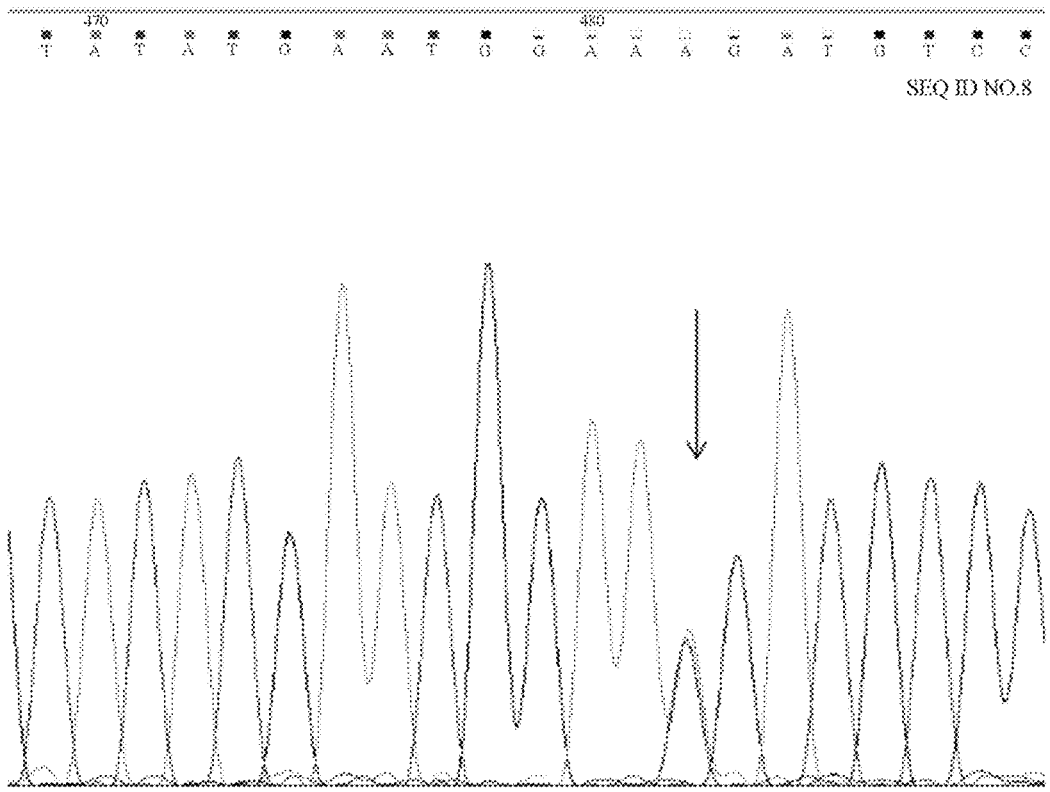
FIG. 3 is a diagram of amplified fragments of the TYR gene in Example 1, wherein the sequence (SEQ ID NO. 8) in the upper part of FIG. 3 is the corresponding base sequence determined according to the sequencing peak map.

The third primer set is used to detect the base type at position 1119 of the TYR gene. As shown by the position pointed by the arrow in FIG. 3, it can be clearly seen that there are overlapping peaks at the pointing place, indicating that there are multiple bases at this position and there is a genetic mutation with a mutation Genotype "c".

Example 2

The difference between Example 2 and Example 1 is only that the selected rabbit breeds are different. In this example, the agouti/Belgian hair color long-hair rabbits are selected as the objects, and other steps are all the same. The method of this example can screen and obtain homozygous genotype Belgian long-haired rabbits to establish a basic group of homozygous genotype Belgian long-haired rabbits.

Example 3

The difference between Example 3 and Example 1 is only that the selected rabbit breeds are different. In this example, the agouti/Belgian hair color rex rabbits are selected as the objects, and other steps are all the same. The method of this example can screen and obtain homozygous genotype agouti/Belgian hair color rex rabbits to establish a basic group of homozygous genotype agouti/Belgian hair color rex rabbits.

Example 4

Figure 4:
FIG. 4 is a diagram showing that the offspring of the unpurified agouti/Belgian hair color meat rabbits have obvious hair color separation.
Figure 5:
FIG. 5 is a diagram showing that the hair colors of the offspring of the purified agouti/Belgian hair color meat rabbits are purely consistent.
Figure 6:
FIG. 6 is a diagram showing that the hair colors of the offspring of the purified agouti/Belgian hair color meat rabbits and the white meat rabbits are the same.

In this example, a population of homozygous agouti/Belgian hair color meat rabbits is obtained following the same steps as in Example 1, and then using them as the hybridization parents or as the breeding material to cultivate specialized breeds. The offspring of agouti/Belgian hair color meat rabbits with the same hair color can be obtained by economically crossing the parental agouti/Belgian hair color meat rabbits with the white meat rabbit parent or the matching line. The results of this example are shown in Table 2 and FIG. 4-6.

TABLE 2

Statistics on Hair Color and Genotype of 298 Offspring from unpurified agouti/Belgian hair color meat Rabbit Intercrossing

| Hair color | total | ASIP genotype | | | MC1R genotype | | | TYR genotype | | |
| --- | --- | --- | --- | --- | --- | --- | --- | --- | --- | --- |
| | | AA | Aa | aa | EE | Ee | ee | CC | Cc | cc |
| white | 50 | 12 | 28 | 10 | 29 | 14 | 7 | 0 | 0 | 50 |
| black | 40 | 15 | 19 | 6 | 0 | 0 | 40 | 14 | 26 | 0 |
| linen | 196 | 133 | 63 | 0 | 140 | 56 | 0 | 76 | 120 | 0 |
| yellow | 12 | 0 | 0 | 12 | 8 | 4 | 0 | 3 | 9 | 0 |

The above examples are only specific examples of the present invention, but the protection scope of the present invention is not limited thereto. Any changes or substitutions that can be easily obtained by those skilled in the art within the technical scope disclosed by the present invention should be covered by the protection scope of the present invention. Therefore, the protection scope of the present invention should be subject to the protection scope of the claims.

What is claimed is:

1. A method for selecting a homozygous genotype agouti hair color rabbit, the method comprising the following steps:
   (1) extracting genomic DNA of a domestic rabbit to be identified, and using a first primer set, a second primer set and a third primer set respectively to amplify to obtain an amplified gene product, the first primer set is used to detect a base sequence of ASIP gene, the second primer set is used to detect a base sequence of MC1R gene, and the third primer set is used to detect a base sequence of TYR gene; and
   (2) according to the amplified gene product obtained in step (1), identifying a genotype of the domestic rabbit to be identified, and the homozygous phenotype agouti hair color rabbit is obtained by selecting, wherein in step (1), a forward primer of the first primer set is 5'-AAGAAAGCAGGAAGGCACA-3' as set forth in SEQ ID NO: 1, and a reverse primer is 5'-CAAGGCAGGATTGGCTCA-3' as set forth in SEQ ID NO: 2;

a forward primer of the second primer set is 5'-ACCTGCTGGTGAGCGTGA-3' as set forth in SEQ ID NO: 3, and a reverse primer is 5'-GTAGCGCAGTGCGTAGAAGA-3' as set forth in SEQ ID NO: 4; and a forward primer of the third primer set is 5'-AAGACAAGGTGAAAGG-3' as set forth in SEQ ID NO: 5, and a reverse primer is 5'-TAAATCCAATAGGCAC-3' as set forth in SEQ ID NO: 6.

2. The method according to claim 1, wherein in step (1), the rabbit to be identified is any one of meat rabbits, rex rabbits, long-hair rabbits, or ornamental rabbits.

3. The method according to claim 1, wherein in step (1), when the first primer set is used for amplification, an amplification system is: a total volume of 20 μL, including Tris-HCL 33.5 mM, $MgCl_2$ 25 mM, dNTPs 0.2 mM, forward primers and reverse primers are 5 ng/μl respectively, Taq DNA polymerase 2.5 U, and template DNA 50 ng; an amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then a PCR amplification program is completed and storing obtained products at 4° C.

4. The method according to claim 1, wherein in step (1), when the third primer set is used for amplification, an amplification system is: a total volume of 20 μL, including Tris-HCL 33.5 mM, $MgCl_2$ 25 mM, dNTPs 0.2 mM, forward primers and reverse primers are 5 ng/μl respectively, Taq DNA polymerase 2.5 U, and template DNA 50 ng; an amplification procedure is: pre-denaturation at 94° C. for 5 minutes; then proceeding 30 cycles of the following steps: denaturation at 94° C. for 45 s, annealing at 52° C. for 45 s, and extending at 72° C. for 30 s; after completing the 30 cycles, extending at 72° C. for 5 min, then a PCR amplification program is completed and storing obtained products at 4° C.

5. The method according to claim 1, wherein in step (2), a identification method is: sequencing the amplified product obtained by using the first primer set, and if a base "A" is detected as an insertion between a 5th position and a 6th position of a second exon of the ASIP gene, it is recorded as Genotype "a", and when the base "A" is not detected, it is recorded as Genotype "A";

sequencing the amplified product obtained by using the second primer set, and if there is no deletion of bases at positions 280-285 of the MC1R gene and a 30 bp deletion of bases at positions 304-333 is detected, it is recorded as Genotype "E"; and sequencing the amplified product obtained by using the third primer set, and detecting a base type at position 1119 of a fourth exon of the TYR gene, when the base is "C", it means that no gene mutation has occurred, thus it is recorded as Genotype "C"; when the base is "A", it means that a gene mutation has occurred, and it is recorded as Genotype "c".

6. The method according to claim 5, wherein the genotype of a homozygous agouti hair color rabbit obtained by selecting is AAEECC.

* * * * *

SEQUENCE LISTING

<160> NUMBER OF SEQ ID NOS: 12

<210> SEQ ID NO 1

<211> LENGTH: 19
<212> TYPE: DNA
<213> ORGANISM: Artificial Sequence
<220> FEATURE:
<223> OTHER INFORMATION: Synthetic

<400> SEQUENCE: 1
aagaaagcag gaaggcaca                                                    19

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
caaggcagga ttggctca                                                     18

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
acctgctggt gagcgtga                                                     18

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gtagcgcagt gcgtagaaga                                                   20

<210> SEQ ID NO 5
<211> LENGTH: 16
<212> TYPE: DNA
<213> ORGANISM: Artificial Sequence
<220> FEATURE:
<223> OTHER INFORMATION: Synthetic

<400> SEQUENCE: 5
aagacaaggt gaaagg                                                       16

<210> SEQ ID NO 6
<211> LENGTH: 16
<212> TYPE: DNA
<213> ORGANISM: Artificial Sequence
<220> FEATURE:
<223> OTHER INFORMATION: Synthetic

<400> SEQUENCE: 6
taaatccaat aggcac                                                       16

<210> SEQ ID NO 7
<211> LENGTH: 20
<212> TYPE: DNA
<213> ORGANISM: Rabbit

<400> SEQUENCE: 7
aggatgaatg gcactcccct                                                   20

```
<210> SEQ ID NO 8
<211> LENGTH: 21
<212> TYPE: DNA
<213> ORGANISM: Rabbit

<400> SEQUENCE: 8
tatatgaatg gaaagatgtc c                                              21

<210> SEQ ID NO 9
<211> LENGTH: 94
<212> TYPE: DNA
<213> ORGANISM: Rabbit

<400> SEQUENCE: 9
tctgctgcct ggccttgtcc gacctgctgg tgagcgtgag cagcgtgctg gagacggccg    60
tcctgctgct gctggtggtg cagcagctgg acga                                94

<210> SEQ ID NO 10
<211> LENGTH: 117
<212> TYPE: DNA
<213> ORGANISM: Rabbit

<400> SEQUENCE: 10
tctgctgcct ggccttgtcc gacctgctgg tgagcgtgag cagcgtgctg ccgtcctgct    60
gctgctggag gcgggcgcct tggccggccg ggccgcagtg gtgcagcagc tggacga      117

<210> SEQ ID NO 11
<211> LENGTH: 88
<212> TYPE: DNA
<213> ORGANISM: Artificial Sequence
<220> FEATURE:
<223> OTHER INFORMATION: Spliced

<400> SEQUENCE: 11
tctgctgcct ggccttgtcc gacctgctgg tgagcgtgag cagcgtgctg gccgtcctgc    60
tgctgctggt ggtgcagcag ctggacga                                       88

<210> SEQ ID NO 12
<211> LENGTH: 117
<212> TYPE: DNA
<213> ORGANISM: Rabbit

<400> SEQUENCE: 12
tctgctgcct ggccttgtcc gacctgctgg tgagcgtgag cagcgtgctg ccgtcctgct    60
gctgctggag gcgggcgcct tggccggccg ggacgcagtg gtgcagcagc tggacga      117
```